(12) United States Patent
Smith et al.

(10) Patent No.: US 8,408,899 B1
(45) Date of Patent: Apr. 2, 2013

(54) DENTAL DELIVERY SYSTEMS, RELATED COMPONENTS AND METHODS

(75) Inventors: Joel P. Smith, Newberg, OR (US); Jonathan E. Myers, Portland, OR (US); Paul H. Johnson, Tigard, OR (US); J. Rick Halbirt, Hubbard, OR (US); Patrick W. Berry, Vancouver, WA (US); Stephen N. Weiler, Dundee, OR (US); Harold Halvorson, Jr., Beaverton, OR (US)

(73) Assignee: A-dec, Inc., Newberg, OR (US)

( * ) Notice: Subject to any disclaimer, the term of this patent is extended or adjusted under 35 U.S.C. 154(b) by 1113 days.

(21) Appl. No.: 11/424,525

(22) Filed: Jun. 15, 2006

Related U.S. Application Data

(60) Provisional application No. 60/691,314, filed on Jun. 15, 2005.

(51) Int. Cl.
*A61C 13/38* (2006.01)
*B01L 9/02* (2006.01)

(52) U.S. Cl. .......................................... 433/77; 312/209

(58) Field of Classification Search .................... 433/77, 433/78–79; 312/209
See application file for complete search history.

(56) References Cited

U.S. PATENT DOCUMENTS

| | | | | |
|---|---|---|---|---|
| 3,217,412 A | * | 11/1965 | Pascente | 433/77 |
| 3,821,852 A | * | 7/1974 | Kato | 433/79 |
| 3,823,475 A | * | 7/1974 | Heubeck | 433/77 |
| 3,986,263 A | * | 10/1976 | Borgelt et al. | 433/99 |
| 4,013,328 A | | 3/1977 | Wolf et al. | |
| 4,026,026 A | * | 5/1977 | Richardson | 433/77 |
| 4,042,287 A | | 8/1977 | Hallen | |
| 4,138,815 A | | 2/1979 | Williams et al. | |
| 4,217,009 A | | 8/1980 | Suter | |
| 4,443,194 A | * | 4/1984 | Fuchs | 433/79 |
| 4,772,200 A | | 9/1988 | Skovsgaard | |
| 4,830,614 A | | 5/1989 | Schricker et al. | |
| 4,934,766 A | | 6/1990 | Schmidt et al. | |
| 4,934,933 A | | 6/1990 | Fuchs | |
| 5,107,636 A | | 4/1992 | Schindele et al. | |
| 5,299,338 A | * | 4/1994 | Foster | 5/658 |
| 5,348,472 A | * | 9/1994 | Joeckel et al. | 433/77 |
| 5,399,007 A | | 3/1995 | Marconet | |
| 5,601,331 A | * | 2/1997 | Austin et al. | 433/79 |
| D458,379 S | | 6/2002 | Brockway | |

OTHER PUBLICATIONS

Stationary. (n. d.). Dictionary.com Unabridged. Retrieved Jul. 27, 2010, from Dictionary.com website: http://dictionary.reference.com/browse/stationary.*
A-dec Equipment Catalog, 2002.
"Centennial Collection Cabinetry," Pelton & Crane, Sep. 2005.
"Dentech Conex Series 2000 Operatory Cabinet System," Dentech Corporation, 2000.
"Fridolin Kompaktplatz Kinderbehandlung," Ultradent, 2005.
"KaVo 34" KRD Rear Delivery System, KaVo America Corporation, 2003.

(Continued)

*Primary Examiner* — Heidi M Eide
(74) *Attorney, Agent, or Firm* — Klarquist Sparkman, LLP

(57) ABSTRACT

Described herein are various embodiments of a dental delivery system. For example, in one exemplary embodiment, a rear dental delivery system through which at least one of water, air and vacuum are delivered for use by a care giver in treating a patient occupying a nearby dental chair can include at least one movable arm that is pivotably mounted to a pivot connection and an upright mounted to the at least one movable arm. The pivot connection can be mounted at approximately a floor level and the at least one movable arm can be configured to pivot slightly above the floor level so as to reduce obstruction in a space separating the dental chair from the dental delivery system.

18 Claims, 12 Drawing Sheets

OTHER PUBLICATIONS

"KaVo 43" KRD Rear Delivery System, KaVo America Corporation, 2003.
"KaVo Portfolio: Your Guide to the World of KaVo Technology," Kavo America Corporation, 2004/2005 edition.
"Midmark Operatory Casework," Midmark Corporation, 2004.
"NextGen Work Stations," Dental EZ Catalog, 2005.
"Procenter Wall & Cabinet Mounted Delivery Units," Midmark Corporation, 2002.
"The Modern Practice: Innovative Products & Technologies for Dental Professionals," Sirona, Oct. 2005.
Promotional Material, "Dentech Advance Cabinet and Wall Units." Copyright 2004.
Promotional Material, "Marus Stellar Cabinets," Marus. "Stellar Cabinets" are pictured on a Feb. 2004, internet-archive webpage (web.archive.org).
Promotional Material, "Control Unit Guide," Engle Dental Systems. Several systems are pictured on an Apr. 2001, internet-archive webpage (web.archive.org).
Promotional Material, "Dental Cabinetry Built for You," Integrated Laminate Systems. Believed to be available at least as early as Jun. 15, 2005.
Promotional Material, "Dentech Conex Heritage Series Cabinets," Dentech Corporation. Believed to be available at least as early as Jun. 15, 2005.
Promotional Material, "Flexible Solutions for Modern Dentistry," Modular and Custom Cabinets. Believed to have been published on or about Jan. 1, 2005 (see brochure reference number of "PIN:MC-CBROCHURE-A-01012005".
Promotional Material, "Cabinet and Wall Mount Dental Units Proma," Royal Dental Group. Model Nos. A5550 and A5560 are referred to on a Jun. 2007, internet-archive webpage.
Promotional Material, "Dansereau," Dansereau. Believed to be available no earlier than 2008.
Promotional Material, "Professional Dental Cabinetry," ILS Dental, pp. 17 and 19. Copyright 2005.
Promotional Material, "Dentech Corporation Equipment Catalog," Dentech Corporation, p. 19. Summer 2005.

* cited by examiner

DENTAL DELIVERY SYSTEMS, RELATED COMPONENTS AND METHODS

CROSS REFERENCE TO RELATED APPLICATION

This application claims the benefit of U.S. Provisional Application No. 60/691,314, filed Jun. 15, 2005, which is incorporated herein by reference.

FIELD

This application relates to dental equipment for practicing dentistry, and in particular to dental delivery systems and related components used in the practice of dentistry.

BACKGROUND

Dental delivery systems refer to the systems used to provide water, air, vacuum, electrical power, etc. for use in dental procedures.

Delivery systems typically encompass a stationary portion (e.g., a mount to a wall, floor, cabinet, dental chair, etc.) and a movable portion allowing a working end of the system to be positioned convenient to the care provider(s) (e.g., dentist, dental assistant, surgeon, etc.) administering treatment to a patient, who typically occupies the dental chair. Known delivery systems are mounted to the dental chair, to an adjacent side wall or cabinet, or to a wall or cabinet located to the rear of the patient, i.e., near the head end of the dental chair (also referred to as the "12 o'clock position"). Side or rear mounted delivery systems are referred to as non-chair mounted delivery systems.

Delivery systems are typically used in most every dental procedure, and they must occupy a portion of the space close to the patient. Therefore, designing delivery systems such that the care providers have optimal workspaces within which they can administer treatment and have the implements and equipment close at hand is important.

Delivery systems include the conduits, lines, connections and implements for supplying water, air and vacuum. Today, such systems also include data lines for communicating data and the associated electronic devices, computer systems and peripherals used by care providers.

At the working end, the delivery system typically has an array of tools and instruments used by the care givers and structures for holding these implements when they are not in use. For general dentistry, these implements would typically include one or more of the following: air/water syringes, vacuum devices, hand pieces (including dental drills), oral cameras, controls for the dental chair and other equipment, displays, etc. These implements may be provided for use at separate locations, i.e., where some are configured for use from the dentist's work position and some from the dental assistant's position, or some commonly used implements may be provided at each work position.

SUMMARY

The present disclosure is directed toward all new and non-obvious features and method acts disclosed herein both alone and in novel and non-obvious combinations and sub-combinations with one another. The disclosure is not limited to constructions which exhibit all of the advantages or components disclosed herein. The embodiments set forth herein provide examples of desirable constructions and are not to be construed as limiting the breadth of the disclosure.

Described herein are various embodiments of a dental delivery system that overcomes at least several of the drawbacks of the prior art. For example, in one exemplary embodiment, a rear dental delivery system through which at least one of water, air and vacuum are delivered for use by a care giver in treating a patient occupying a nearby dental chair can include at least one movable arm that is pivotably mounted to a pivot connection and an upright mounted to the at least one movable arm. The pivot connection can be mounted at approximately a floor level and the at least one movable arm can be configured to pivot slightly above the floor level so as to reduce obstruction in a space separating the dental chair from the dental delivery system.

In some implementations, the rear dental delivery system can include a work surface coupled to the upright. In specific implementations, the work surface can be generally circular and pivotably coupled to the upright at a pivot point spaced apart from a central axis of the work surface. In specific implementations, the work surface has a periphery with at least a portion of the periphery being curved. The work surface can be pivotably coupled to the upright at a pivot point positioned near the periphery. In yet certain implementations, an auxiliary tool holder can be selectively positionable along an edge of the work surface.

In certain implementations, the delivery system can include a housing positioned adjacent a junction between the at least one movable arm and the upright.

In specific implementations, an arm can be pivotably coupled to the work surface and comprise a tool holder that is movably coupled to the arm. The tool holder can have at least one movable tool clamp. In at least one implementation, the tool holder includes a control pad that is capable of controlling at least one dental chair function.

In some implementations, the rear dental delivery system can include a second upright that can be positioned closer to the pivot connection than the first mentioned upright. In certain implementations, the second upright can support an extension arm that is movable relative to the second upright. In specific implementations, the first upright supports implements generally used by a dental assistant and the second upright supports implements generally used by a dentist or dental hygienist.

In certain implementations, the second upright is coupled to the first upright at a point spaced above the at least one arm. The delivery system can also include a housing that covers a junction between the at least one movable arm, the first upright and the second upright. The second upright can be coupled to the first upright in a spaced apart relationship via a bracket.

In certain implementations, the pivot connection of the rear dental delivery system is positioned rearwardly and approximately aligned with a head end of a dental chair. In specific implementations, the pivot connection is positioned adjacent a cabinet and does not extend above a level of cabinet access openings, thereby allowing the cabinet access openings to be accessed while rear dental delivery system is installed. In specific implementations, the dental chair is a reclineable dental chair and, when in the reclined position, a distance between the dental chair and the cabinet is between approximately 20 inches and approximately 26 inches.

In some implementations, the distance between the floor level and the at least one movable arm is less than approximately six inches. In some implementations, the pivot connection includes an attachment portion configured for attachment to a horizontal surface.

In certain implementations, the delivery system includes air and vacuum connections extending through the pivot connection, the at least one movable arm and the upright.

According to one exemplary embodiment, a rear dental delivery system through which at least water, air and vacuum are delivered for use by a care giver in treating a patient occupying a nearby dental chair can include at least one movable arm pivotably mounted to a pivot connection positioned substantially at a floor level. The delivery system can also include an upright mounted to the at least one movable arm and a work surface mounted at an off-center location to the upright. The work surface can have a periphery where at least a portion of the periphery is curved. An arm can be pivotably mounted to an approximate center of an underside of the work surface and protruding beyond the curved periphery. The arm can assist in holding implements used by the care giver in convenient storage positions.

One exemplary embodiment of a method of delivering water, air and a vacuum line to a dental operatory having a dental chair and a rear area adjacent a head end of the chair can include pivotably mounting a swing arm to pivot close to a horizontal surface at a step-over height. The method can also include mounting an upright member to the swing arm proximate a distal end of the swing arm. The method can further include mounting a work surface to the upright member to pivot about a location offset from a central axis of the work surface. The work surface can be elevated above the swing arm and a knee space accommodating a seated practitioner can be defined below the work surface and above the swing arm.

The foregoing and other features and advantages will become more apparent from the following detailed description, which proceeds with reference to the accompanying figures.

DETAILED DESCRIPTION

Figure 1:
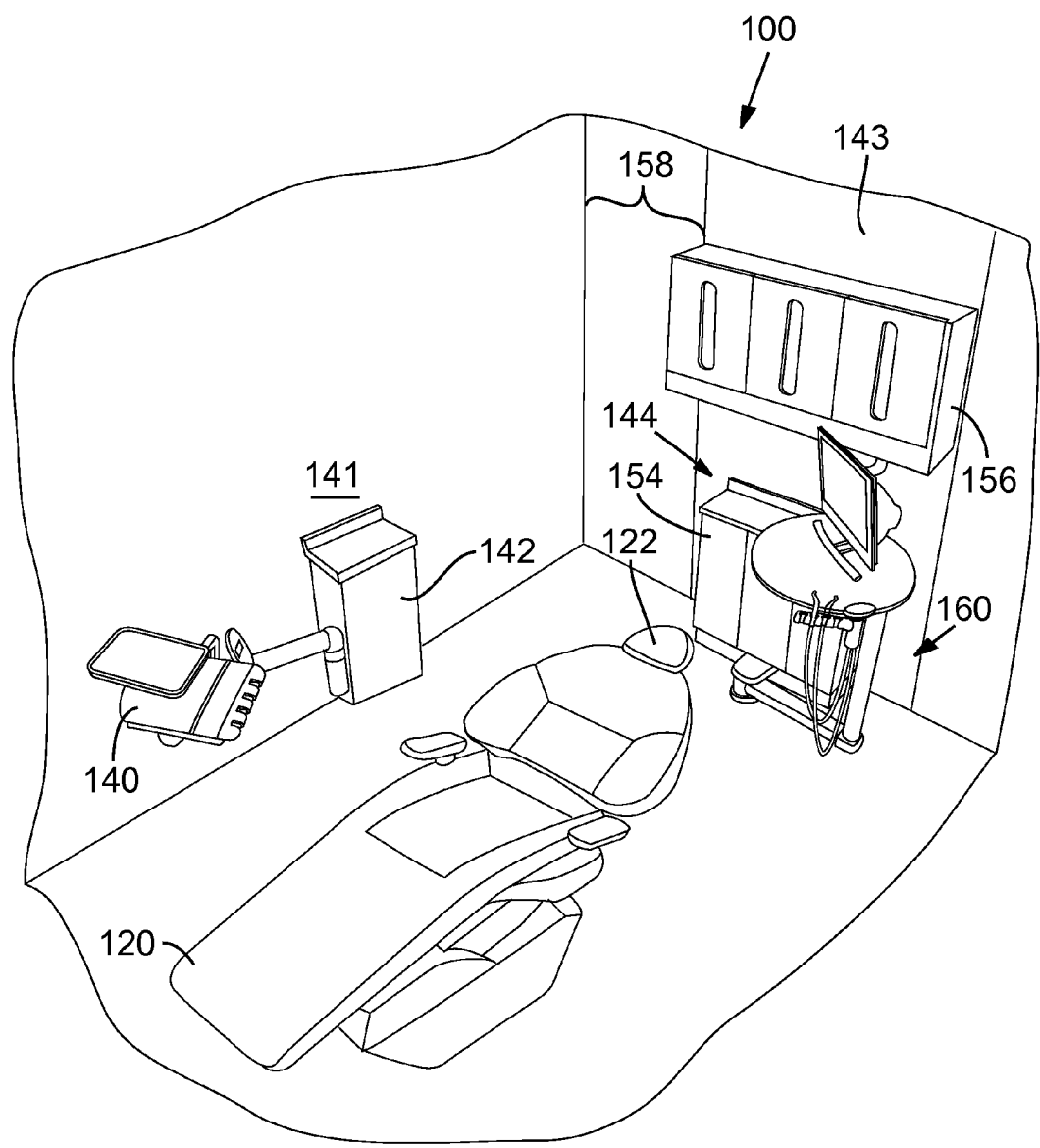
FIG. 1 is a perspective depiction of one exemplary embodiment of a dental operatory having a side mounted delivery system and a rear mounted delivery system.

Described herein are various embodiments of rear and side mounted dental delivery systems suitable for use in a dental operatory. For example, in FIG. 1, an exemplary embodiment of a dental operatory 100 having a dental chair 120, side mounted delivery system 140 and a rear mounted delivery system 160. The operatory 100 can have an opening 158 between the end of a rear wall 143 and an adjacent side wall 141. This represents one possible doorway for care providers and patients to access the operatory 100. Of course, the doorway may be positioned at another location, or there may be multiple doorways.

As shown, the side mounted delivery system 140 can be positioned to one side of the dental chair 120, which is shown in the reclined position, and the rear mounted delivery system 160 can be positioned to the rear of the dental chair, i.e., adjacent its head end 122, or approximately at the twelve o'clock position.

The side mounted delivery system 140, which typically includes the implements used by the dentist, is pivotally attached to a wall 141, such as via a cabinet 142, adjacent the chair 120 as shown. In FIG. 1, the side mounted delivery system 140 is shown in a storage position, which is spaced apart from the dental chair to provide a walkway for care providers and patients. When in use, the side mounted delivery system 140 is typically pivoted to a position closer to the dental chair 120 (see FIG. 12).

Figure 3:
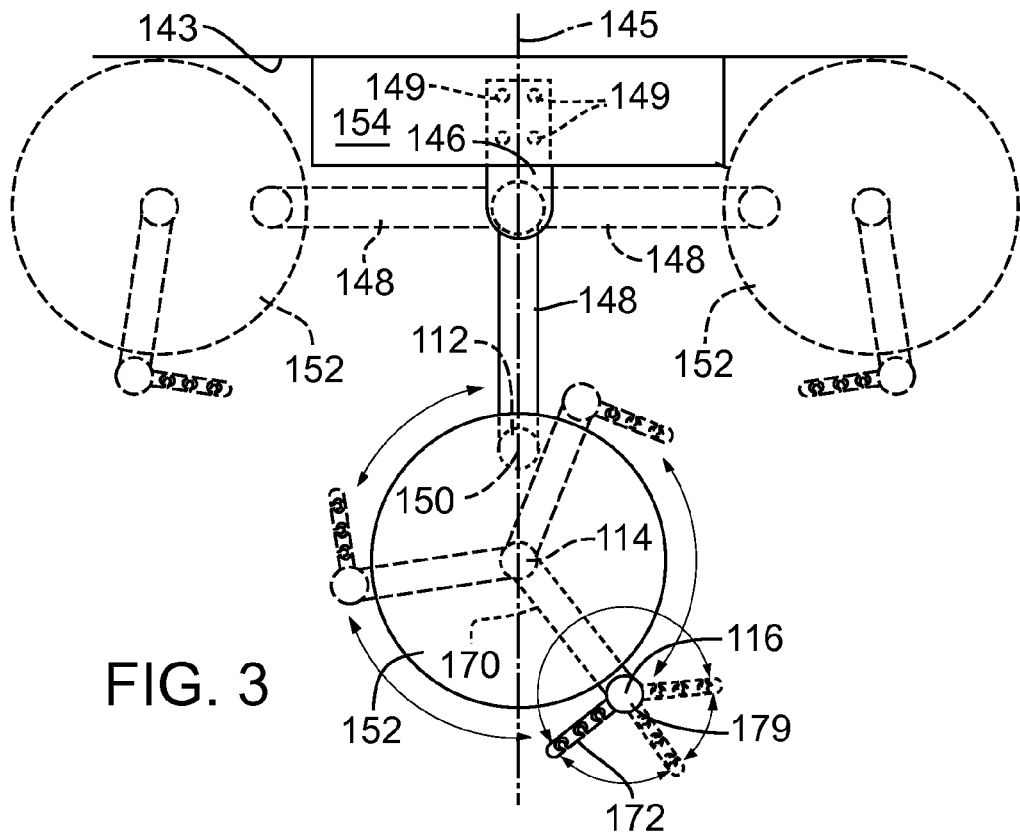
FIG. 3 is a plan view of the rear mounted delivery system of FIG. 1 in various configurations as depicted by dashed lines.

In relation to the dental chair 120, the rear mounted delivery system 160 is pivotably attached to an adjacent rear wall 143 or cabinet, such as the cabinet 144, at a rear centerline, or 12 o'clock position, indicated at 145 in FIG. 3. Although not specifically shown, the operatory 100 need not have a cabinet attached to the rear wall 143 and the rear mounted delivery system can extend transversely from the rear wall. In some implementations having a cabinet attached to the rear wall 143, such as cabinet 144, the cabinet can have separate portions, such as a lower cabinet 154 and an upper cabinet 156 as shown in FIG. 1, or it may be a single structure such as is shown, for example, in FIG. 14.

Figure 2:
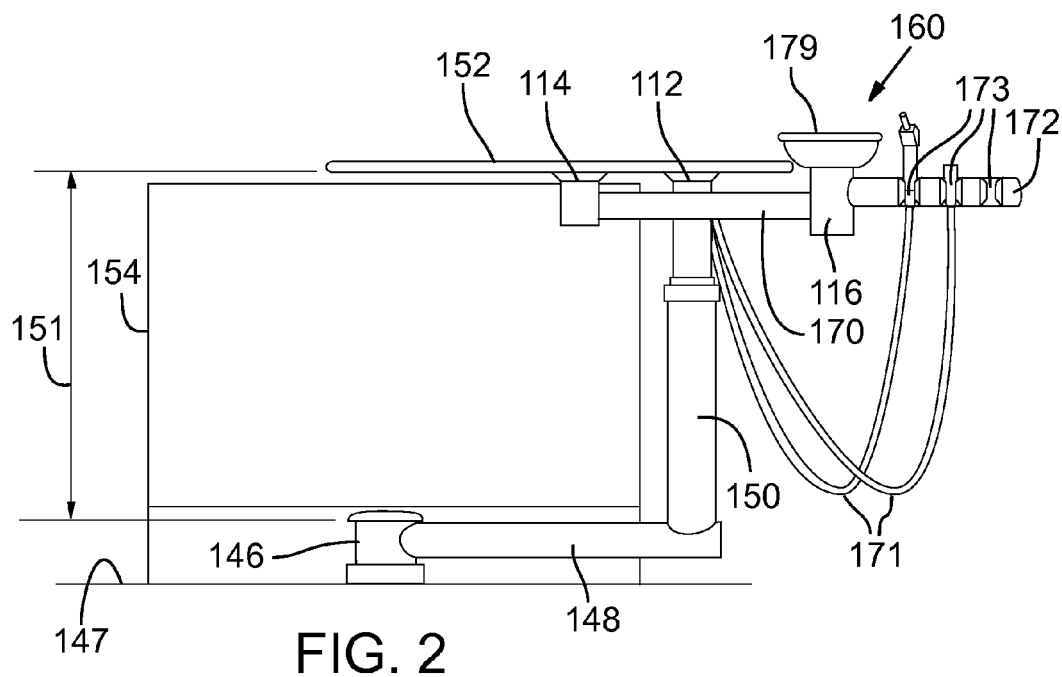
FIG. 2 is an enlarged elevational view of the rear mounted delivery system of FIG. 1 shown mounted adjacent a cabinet.

Referring to FIG. 2, the rear mounted delivery system 160 has a pivot connection 146, a pivotable arm 148, an upright 150 attached to the arm 148, a work surface 152 supported by the upright 150, and an arm 170 pivotably supported by the work surface.

Preferably, the pivot connection 146 is generally positioned at a low level, e.g. near the level of the floor 147 as shown. In the exemplary implementations, a stationary, or attachment portion, of the pivot connection 146 is mounted to a secure stationary horizontal surface, such as the floor 147, by fasteners, such as fasteners 149 (see FIG. 3). Alternatively, or in addition to mounting the stationary portion of the pivot connection 146 to the floor, the stationary portion can be mounted to a cabinet, such as cabinet 144, which in turn is securely mounted to a stationary and secure object, such as a wall and/or a floor.

The pivot connection 146 can be mounted to the floor such that a portion of the connection is positioned at least partially underneath the cabinet 154 and a portion extends transversely away from the cabinet. The arm 148 can be pivotably coupled to the portion extending away from the cabinet and be generally horizontal as shown. This configuration of the pivot connection 146 and the arm 148 provides sufficient ease and flexibility in repositioning equipment, but increases the work space available to the care providers by positioning the arm and pivot connection away from the areas of their knees and hips. For example, a leg and knee space 151 defined between the underside of the work surface 152 and the upper surface of the support arm 148 can allow for uninhibited movement of a care provider's legs into various positions required for operation on a patient.

In some implementations, the horizontal extent of the arm 148 can be about as great as one half the width of the cabinet. In other implementations, the arm is longer than one half the width of the cabinet. Of course, the arm could be shorter than one half the width of the cabinet.

Figure 16:
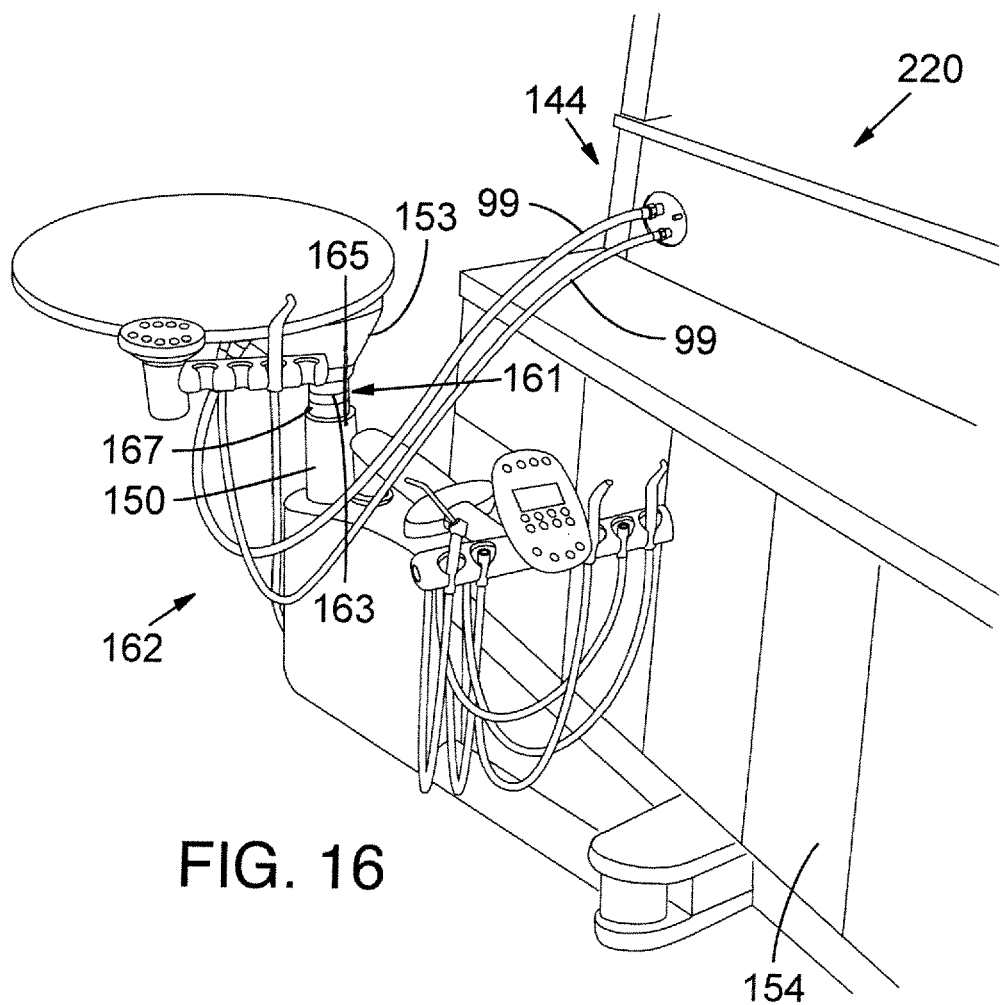
FIG. 16 is a perspective view of a dental line cleaning system integrated in a cabinet and suitable for use with a rear mounted delivery system.

The upright 150 pivotably supports at least one member, such as work surface 152, extending laterally and capable of supporting equipment. In the illustrated implementations, the work surface 152 is pivotably supported by the upright 150 and extends horizontally relative to the ground. As illustrated, a pivot connection 112 defining a pivot point, which can be positioned at the approximate center of the pivot connection, can couple the work surface to the upright and be coupled to an underside of the work surface at a location offset from the center of the work surface. As shown in FIG. 16, in some embodiments, the pivot connection 112 can include a structural member 153, which can also act as a cover.

In the illustrated embodiments, the work surface 152 can be raised or lowered as desired. For example, as shown in FIG. 16, the upright 150 can include an adjustment mechanism 161 for conveniently adjusting the height of the work surface 152 relative to the arm 148 or ground level. The adjustment mechanism 161 can include a cylindrical portion 163 insertable into a top portion 165 of upright 150. The cylindrical portion 163 can have multiple axially displaced external grooves mateable with a bracket 167 having an annular tooth or protrusion portion and being removably attachable to the cylindrical portion. When attached, the tooth portion of the bracket 167 is matingly received in a respective groove of the cylindrical portion 163 thus preventing the bracket from movement in the axial direction. The cylindrical portion 163 is lowered into the top portion 165 of upright 150 until the bracket 167 contacts the upright to prevent the cylindrical portion from movement in the downward direction. The work surface 152 is adjustable by matingly attaching the bracket 167 to one of the grooves associated with the desired height of the work surface. In other implementations, the adjustment mechanism can be another type of mechanism, such as a ratcheting type mechanism, commonly known in the art.

As shown in the exemplary implementations, the arm 170 is pivotably supported by the work surface 152 via a pivot connection 114 defining a pivot point, which can be at an approximate center of the pivot connection. In the illustrated embodiments, the pivot connection 114 between the arm 170 and the work surface 152 is located on the underside of the work surface at its approximate center. The arm 170 can support a tool holder 172 as shown. In some implementations, the tool holder 172 can be pivotably supported by the arm 170 via a pivot connection 116 defining a pivot point, which can be at an approximate center of the pivot connection. In some embodiments, the pivot connection 116 is coupled to the tool holder 172 at a location midway along the length of the tool holder 172, while in the illustrated embodiments, the pivot connection is coupled to the tool holder proximate one of the two ends of the tool holder. Moreover, a control, or touch, pad 179 for controlling various characteristics of the system can be mounted to the pivot connection 116 or directly to the tool holder 172.

The non-chair mounted delivery systems, i.e., the side mounted delivery system 140 and the rear mounted delivery system 160, are preferred by some care providers for providing space-saving benefits. For example, when a side mounted delivery system is provided, it typically replaces a chair mounted system. Similarly, when a rear mounted delivery system is provided, it also typically replaces a chair mounted system. Of course, it would be possible to use one or both of the delivery systems 140 and 160 in conjunction with a chair mounted delivery system if desired.

Figure 4:
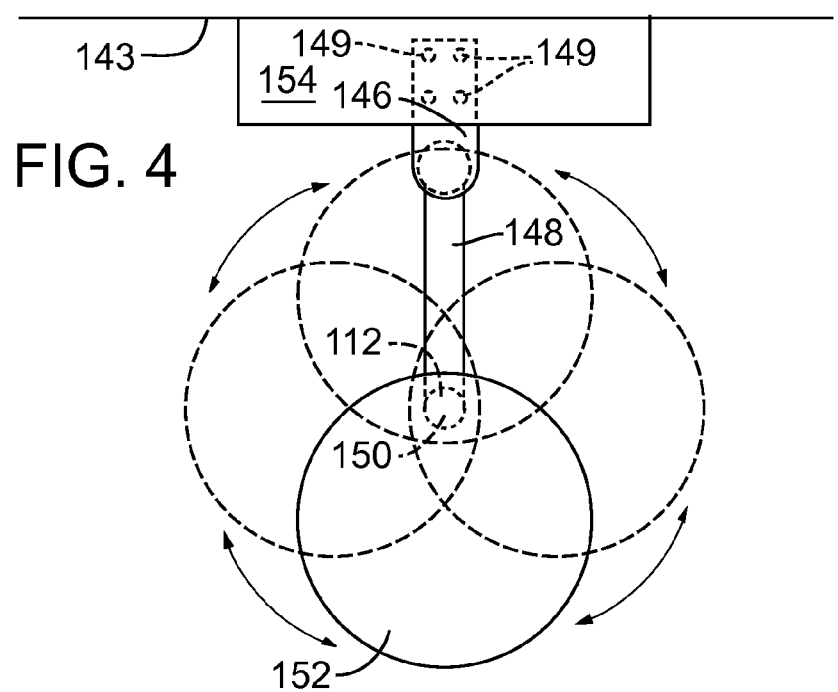
FIG. 4 is a plan view of the rear mounted delivery system of FIG. 1 showing the work surface in various configurations as depicted by dashed lines with certain components of the delivery system not shown for clarity.

Of particular value is the ability of a user to customize the positioning of one or more of the various components of the rear and side mounted dental delivery systems described herein. More specifically, the increased range of motion of the rear mounted delivery system results in better visibility, less stretching and reduced extraneous motion for a user of the delivery system. Further, the multi-tiered or multi-layered approach to positioning the various components of the rear mounted delivery system provides additional customizability, convenience and space-saving benefits over conventional delivery systems. FIGS. 3 and 4 show some of the possibilities for positioning the rear delivery system 160 and its components.

In FIG. 3, the arm 148 has been pivoted approximately 90-degrees about pivot connection 146, which defines a pivot point, from the position of the arm shown in FIG. 1 (also indicated in dashed-line in FIG. 3 as extending generally parallel to the cabinet and to the right of the pivot connection 146) such that the arm extends generally transversally from the cabinet 144. The arm 148 can be pivoted from this position to a position in which the arm extends generally parallel to the cabinet and to the left of the pivot connection 146 as indicated in dashed-line in FIG. 3. As can be recognized, the arm 148 also can be pivoted into any position intermediate the positions shown in FIG. 3. In other words, the arm 148 can be pivoted, or rotated, about pivot connection 146 into any position within a range of about 180 degrees.

The ability to pivot the arm 148 to either side can be used, among other purposes, to adapt the rear delivery system for use by right-handed or left-handed care providers. Further, the pivot arm 148 can be positioned at an intermediate point between the two extremes as shown in FIG. 3, which is a position that might be used when the head end of the chair remains elevated (see FIG. 11).

As shown in FIG. 3, arm 170 is pivotable approximately 270-degrees about pivot connection 114 independent of pivot arm 148. In other implementations, however, the arm 170 can be pivotable more or less than 270-degrees about pivot connection 114. Likewise, the tool holder 172 is pivotable about pivot connection 116 independent of pivot arm 148 and arm 170. As shown, in some implementations, the tool holder 172 is pivotable approximately 270-degrees about pivot connection 116. In some implementations, however, the tool holder 172 is pivotable more or less than 270-degrees about pivot connection 116. In some embodiments, the arm 170 and the work surface 152 can be sized as shown such that the tool holder 172 remains close to the edge of the work surface and conveniently within grasp.

In some implementations, the tool holder 172 includes multiple tool clamps 173 (e.g., as shown in FIG. 2) placed laterally along an axis of the tool holder 172. Each tool clamp 173 is configured to removably secure a single dental implement as shown, or multiple implements in other implementations. The tool clamps 173 can be individually movable relative to an axis of the tool holder 172, such as by being rotatable about the axis of the tool holder, and sustainable in one of various positions about the axis by an internal latching mechanism (not shown). In this manner, the tool clamps can be rotated independently of each other to place a respective implement in a desired and convenient orientation for access by a user.

Referring to FIG. 4, the work surface 152 is pivotable approximately 360-degrees about pivot connection 112 independent of pivot arm 148, arm 170 and tool holder 172.

As has been described, the pivot arm 148, work surface 152, arm 170, tool holder 172 and tool clamps 173 can be movable independently of each other. In other words, the rear delivery system 160 shown in FIGS. 1-4 can be described as having five degrees of adjustability or positionability.

Figure 5:
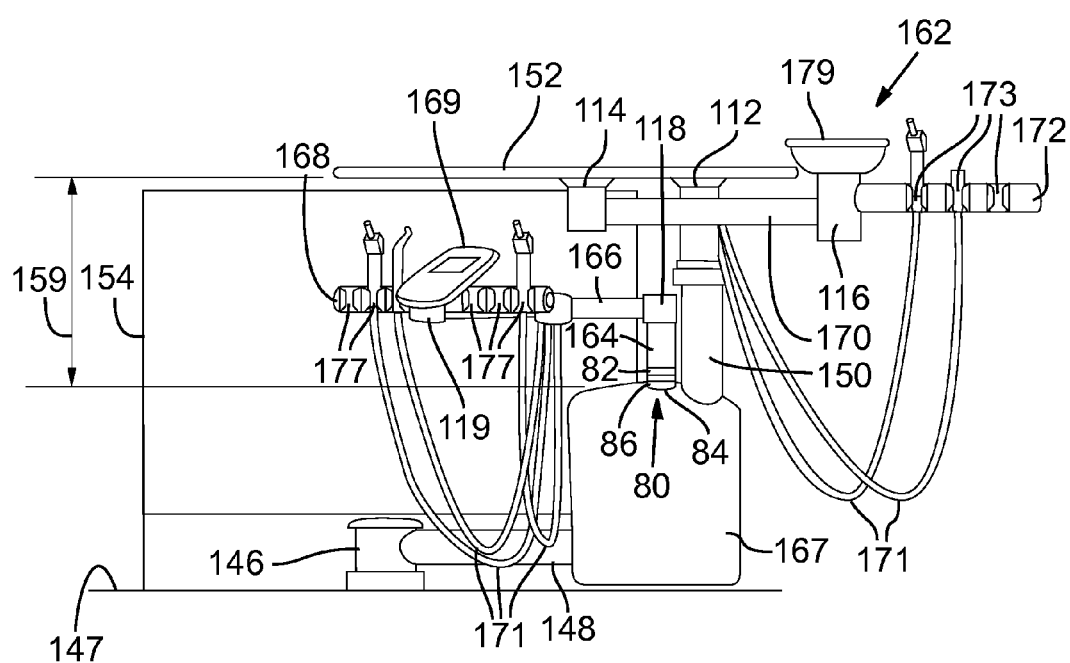
FIG. 5 is an elevational view of an exemplary embodiment of a rear mounted delivery system mounted to a cabinet and having a second upright member.

While FIG. 1 shows a configuration in which there is a separate side mounted delivery system 140 specifically configured for use by, for example, a dentist (or hygienist), and a rear mounted delivery system 160 specifically configured for use by, for example, a dental assistant (or hygienist), FIG. 5 shows a two-position rear delivery system 162 designed to provide two work positions, i.e., the work position for the hygienist or assistant and the work position for the dentist or hygienist, as well as the required implements used in each position.

In the illustrated embodiments, the rear delivery system 162 includes some features that are similar to the features of rear delivery system 160. Corresponding similar features have matching reference numerals unless otherwise noted.

The rear delivery system 162 includes a second upright 164. In some implementations, the second upright 164 is attached to the arm 148 and, in the illustrated implementations, the second upright 164 is coupled to the upright 150 via a bracket 175 (see FIG. 13). As perhaps best shown in FIG. 5, a cover 167 can be positioned as shown to at least partially enclose an interior 181, which as will be discussed below in greater detail, can include the bracket 175 (see FIG. 13). A knee space 159 defined between the underside of the work surface 152 and the upper surface of the cover 167 can allow for uninhibited movement of a care provider's knees into various positions during operation on a patient.

As shown, the second upright 164 pivotably supports an extension arm 166 at an upper end via a pivot connection 118 defining a pivot point, which can be at the approximate center of the pivot connection. Alternatively, in some implementations, the upright 164 and extension arm 166 are integrally formed, i.e., formed of a one-piece monolithic construction, and the upright 164 is pivotably coupled to the upright 150, such as via bracket 175 (see FIG. 13) or support arm 148.

The extension arm 166 can pivotably support a tool holder 168 via a pivot connection 119 defining a pivot point, which can be at the approximate center of the pivot connection. The pivot connection 119 can be coupled to the tool holder 168 at one of the ends of the tool holder or at a location intermediate its ends. Moreover, a control, or touch, pad 169 for controlling various characteristics of the system can be mounted to the pivot connection 119 or directly to the tool holder 168.

Similar to the upright 150, the height of the second upright 164 and thus the extension arm 166 and tool holder 172 can be adjusted. For example, as shown in FIG. 5, the upright 164 can include an adjustment mechanism 80 for conveniently adjusting the height of the extension arm 166 relative to the arm 148 or ground level 147. The adjustment mechanism 80 can include a cylindrical portion 82 insertable into an opening 84 in the cover 167. The cylindrical portion 82 can have multiple axially displaced external grooves mateable with a toothed bracket 86 removably attachable to the cylindrical portion. When attached, the bracket 86 contacts a second upright mounting bracket 175, as will be described in more detail below, to prevent the cylindrical portion 82 from movement in the downward direction. The extension arm height is adjustable by matingly attaching the bracket 86 to one of the grooves associated with the desired height of the extension arm 166. In other implementations, the adjustment mechanism can be another type of mechanism, such as a ratcheting type mechanism commonly known in the art.

Figure 6:
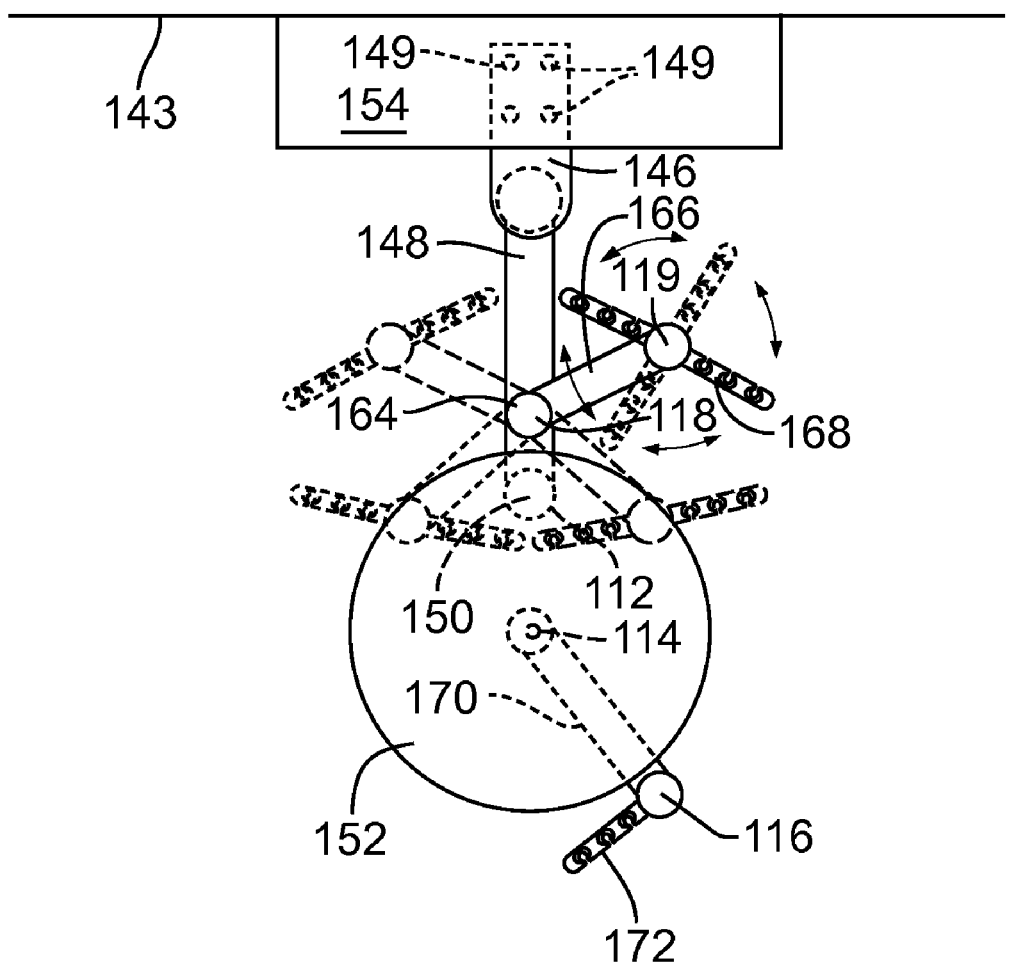
FIG. 6 is a plan view of the rear mounted delivery system of FIG. 5 in various configurations depicted by dashed lines.

In addition to the same possibilities for positioning the arm 148, arm 170, tool holder 172 and work surface 152 as described above in relation to rear delivery system 160, the rear delivery system 162 is also capable of other positioning possibilities. For example, as shown in FIG. 6, the extension arm 166 is pivotable about pivot connection 118 independently of the pivot or support arm 148, work surface 152, arm 170 and tool holder 172. In the illustrated implementation, the extension arm 166 is rotatable approximately 180-degrees about pivot connection 118 with complete rotation being inhibited by first upright 150.

Referring again to FIG. 6, in one specific implementation, the tool holder 168 is rotatable about pivot connection 119 independently of arm 148, work surface 152, arm 170, tool holder 172 and extension arm 166. Further, similar to tool holder 172, tool holder 168 can have multiple independently movable tool clamps 177 (see FIG. 5) for removably securing dental implements.

As has been described, the pivot arm 148, work surface 152, arm 166, tool holder 168, arm 170, tool holder 172 and tool clamps 177 can be movable independently of each other. In other words, the rear delivery system 162 shown in FIGS. 5 and 6 can be described as having seven degrees of adjustability or positionability.

As indicated generally at 171 in FIGS. 2 and 5, various implements and their associated conduits and cables, can be positioned as shown relative to the holder 172 and the holder 168. Each one of the various implements and associated conduit or cable can provide, for example, a fluid, such as air and water, or a vacuuming line. Desirably, at least a portion of the conduits and cables extend through at least one of the members, e.g., the arm 148, the upright 150, the arm 170, the second upright 164, the arm 166. In some implementations, at least some of the conduits and cables extend through at least one of the pivot connections, or arm connectors, 110, 112, 114, 116, 118, 119. In this manner, portions of the cables and conduits can be hidden or contained within the arms and arm connectors to minimize extraneous exposure of cables and conduits to dentists, dental assistants and patients.

Figure 7:
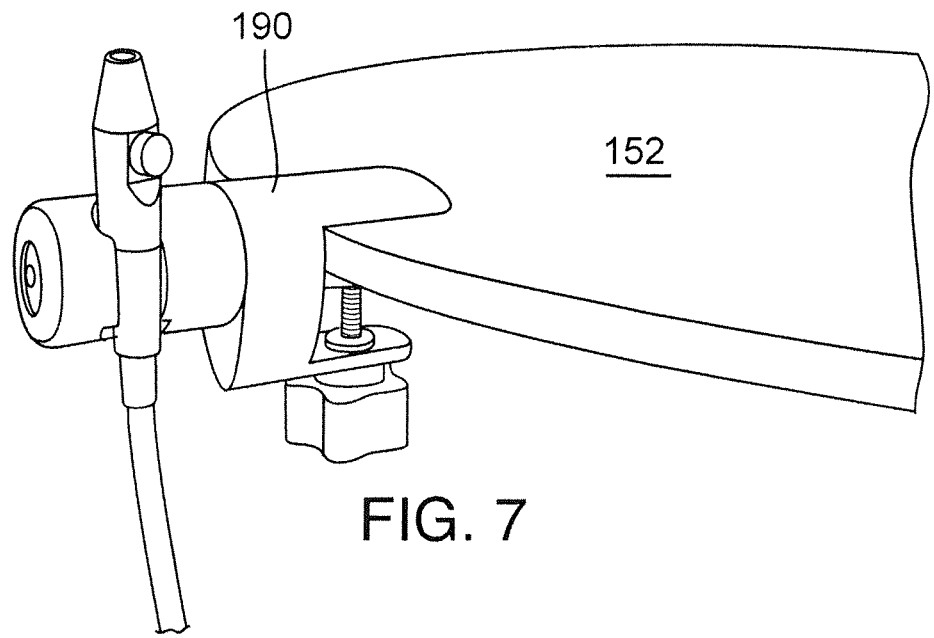
FIG. 7 is a perspective view of an auxiliary tool holder removably attached to a work surface of a rear mounted delivery system.

Optionally, in some implementations, the rear delivery system as described herein can include an auxiliary tool holder 190, as shown in FIG. 7, which is adapted for temporary attachment at any point along the periphery of the work surface 152.

Figure 8:
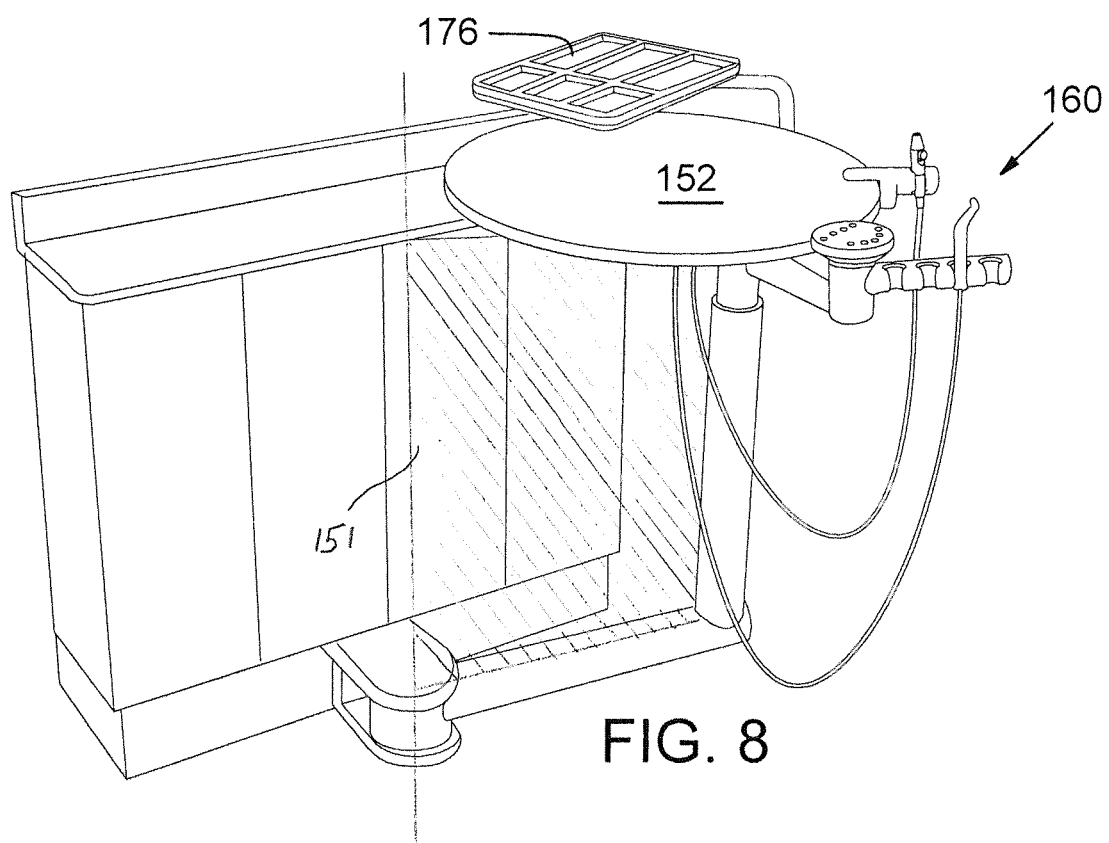
FIG. 8 is a perspective view of an auxiliary tray movably attached to a work surface of a rear mounted delivery system.

Referring to FIG. 8, the rear mounted delivery system, e.g., delivery system 160, can have additional components, such as auxiliary tray 176, to provide added flexibility in positioning the rear delivery system. Auxiliary tray 176 is pivotally connected to an edge of the work surface 152 for positioning above the work surface.

Figure 9:
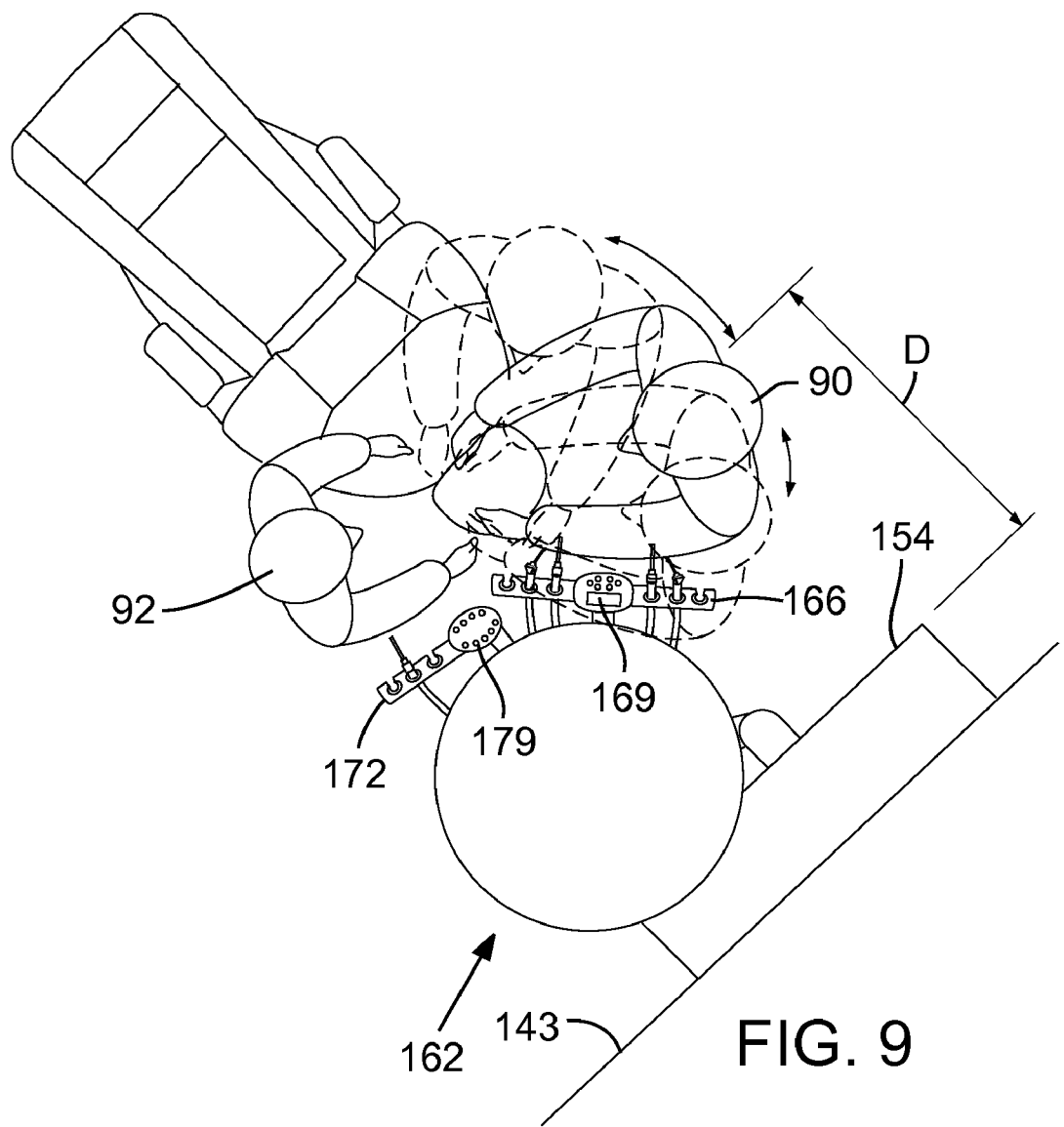
FIG. 9 is a partial plan view of an exemplary dental operatory showing a dental assistant and dentist in a variety of positions relative to the dental chair and the rear mounted dental delivery system.
Figure 10:
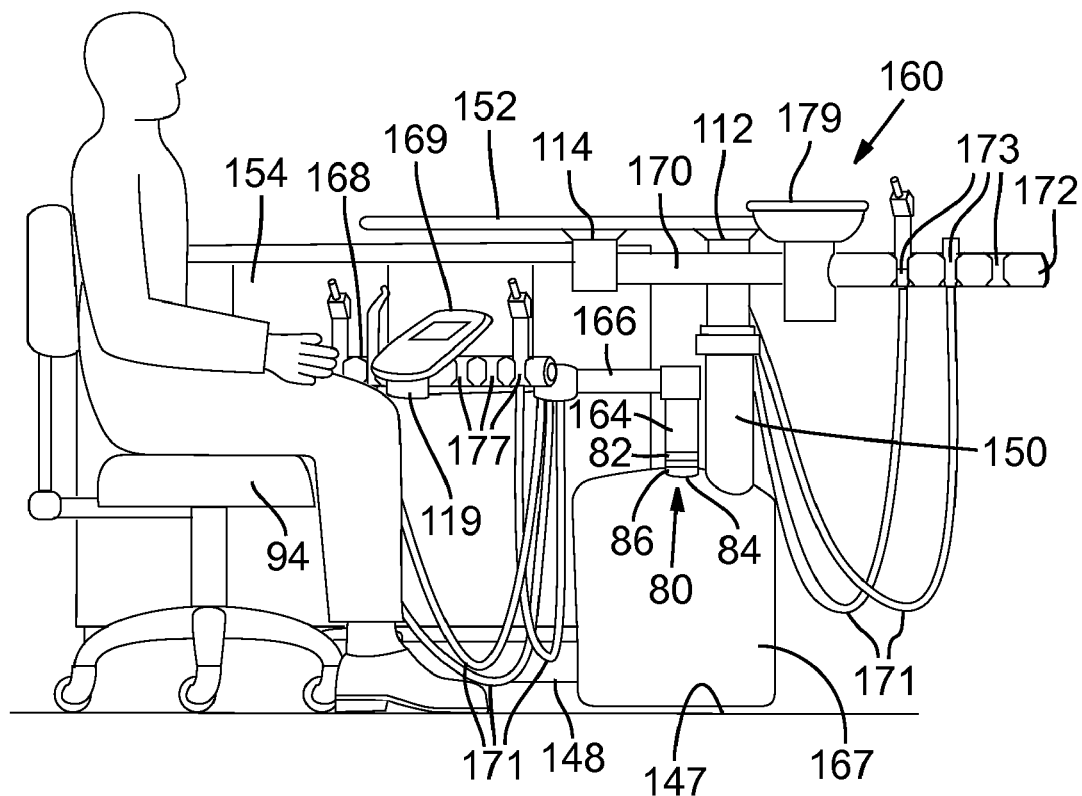
FIG. 10 is an elevational view of an exemplary dental operatory having a rear mounted dental delivery system, dental chair, dentist chair and cabinet.

FIGS. 9 and 10 show the rear delivery system, which in this example is delivery system 162, in use during a range of typical dental procedures to illustrate the functionality of the various components. In the figures, FIG. 90 is portraying the dentist's role, and FIG. 92 is portraying the dental assistant's role.

Referring to FIG. 9, it can be seen that the extension arm 166 (obscured in the figure) has been positioned such that the tool holder 168 is conveniently positioned for the dentist 90 and the tool holder 172 is conveniently positioned for the dental assistant 92.

As shown in solid lines, the dentist 90 is operating from a 10 o'clock position relative to the patient. The dentist 90 can move to his left from the 10 o'clock position to the 11 o'clock position, indicated in dashed lines, without requiring the assistant to change her position or the position of the work surface 152. Although not specifically shown, the work surface 152 and tool holder 168 can be moved from the position shown in FIG. 9 such that the dentist 90 can operate from the 12 o'clock position and freely move between the 12 o'clock position and the 10 o'clock position without requiring repositioning of the work surface or tool holder.

In some specific implementations, the operatory 100 of FIG. 1 can be configured such that a distance D between the cabinet 154 and the head end 122 of the chair 120 (see FIG. 9) is between approximately 20 and 26 inches. Such a distance D allows the dentist 90 or assistant 92 to easily position him/herself in the 12 o'clock position between the cabinet and the dental chair 120. Further, as shown, the dentist 90 also can move to his/her right from the 10 o'clock position to about the 8 o'clock position, indicated in dashed lines, relative to the patient. In other words, in some implementations, the dentist 90 can move between various positions relative to the patient without requiring adjustment of any of the various components of the rear dental delivery system.

Since the arm 148 is at a step-over height, i.e., between zero and six inches, the arm does not impede movement of the dentist 90 by blocking the dentist's legs. More specifically, the leg or knee spaces 151, 159 allow a dentist's or assistant's legs to move freely between the arm 148 and the work surface 152 as the dentist or assistant moves between various positions relative to a patient. For example, as perhaps best shown in FIG. 10, dentist 90 is sitting on a conventional chair, or stool, 94 in an operating position. When in the operating position and while sitting down, there is sufficient clearance between the arm 148 and the work surface 152 such that the dentist can freely position his legs between the arm and the work surface without undesirable contact with the components of the rear delivery system or requiring adjustment of the delivery system.

Alternatively, if desirable, as the dentist 90 moves from one position to another, such as from the 11 o'clock position to the 8 o'clock position, he can grab and pivot the arm 166 toward him to provide him more convenient access, e.g., to the tool holder 168. As also shown in FIG. 9, the assistant 92 has the tool holder 172, and specifically the control pad 179, positioned within convenient reach of her right hand.

Figure 11:
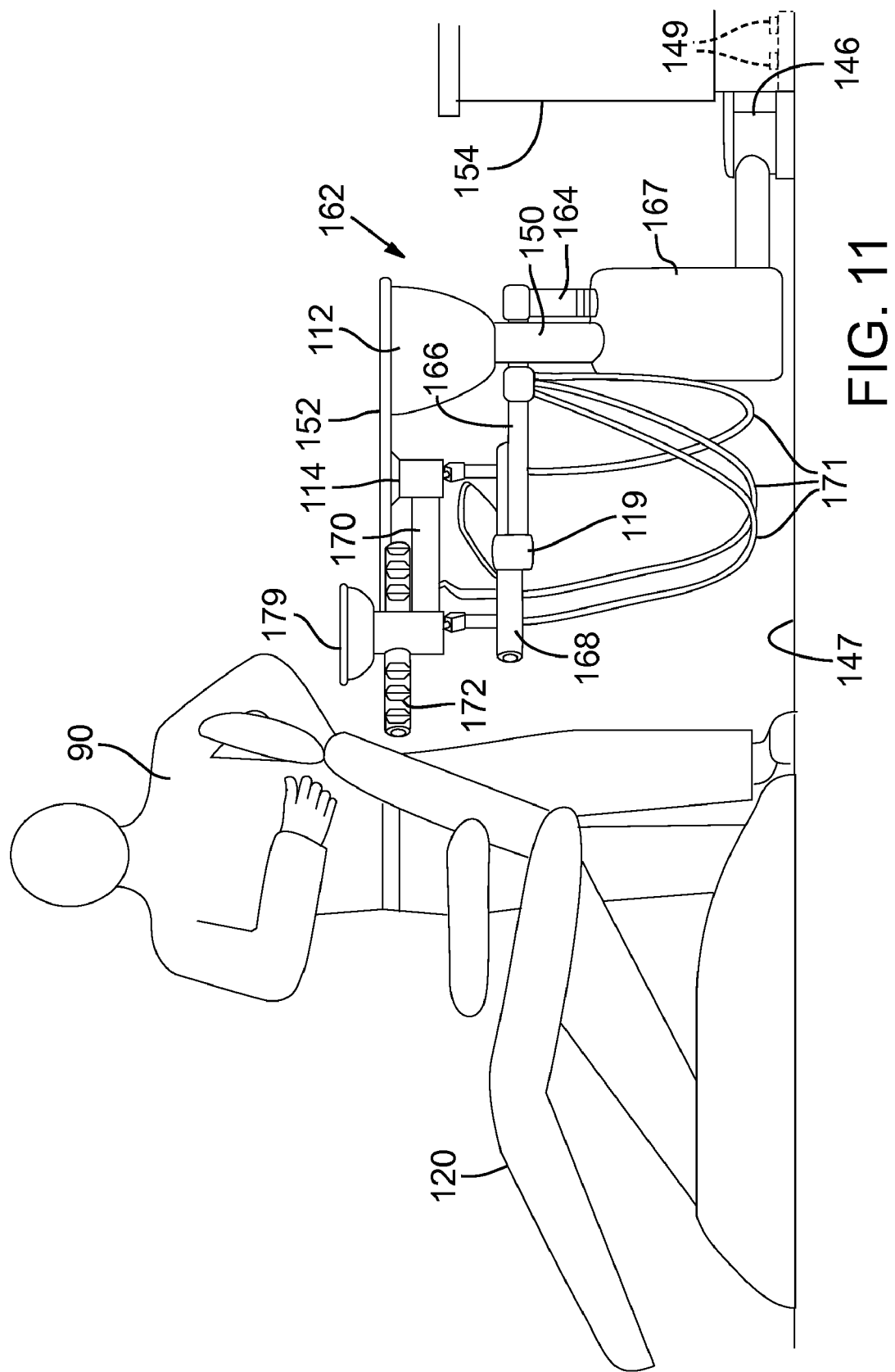
FIG. 11 is an elevational view of the dental operatory of FIG. 9 showing the dentist in a standing position and the dental chair in an inclined position.

Now referring to FIG. 11, the dentist 90 is operating from a standing position instead of a seated position, such as during treatment of a patient who cannot be reclined. As shown, with the dentist chair 120 in the inclined position, the arm 148 has been swung to an intermediate position, e.g., approximately transverse to the cabinet 154, such that the work surface 152 and the tool holder 168 remain within convenient reach. With the arm 148 in the intermediate position, an assistant (not shown) in the standing position can conveniently reach the tool holder 172.

Figure 12:
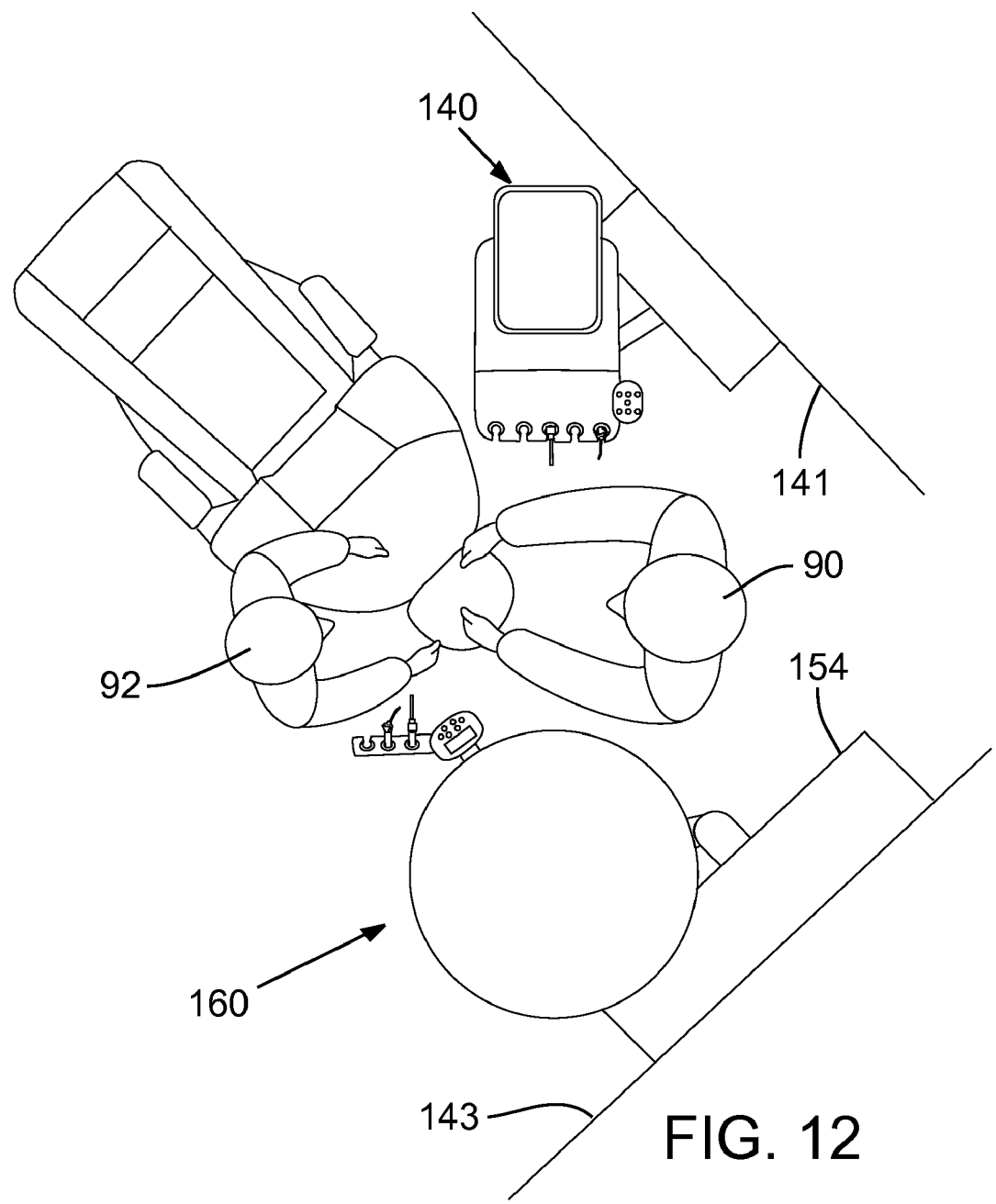
FIG. 12 is a plan view of the dental operatory of FIG. 1 shown with the side mounted dental delivery system extended for use by a dentist.

FIG. 12 shows an exemplary position of the rear mounted delivery system 160 and side mounted delivery system 140 in use. As shown, the dentist 90 is using the tools held by the side mounted delivery system 140 and the dental assistant 92 is using the tools held in the tool holder 172 of the rear mounted delivery system 160.

Figure 13:
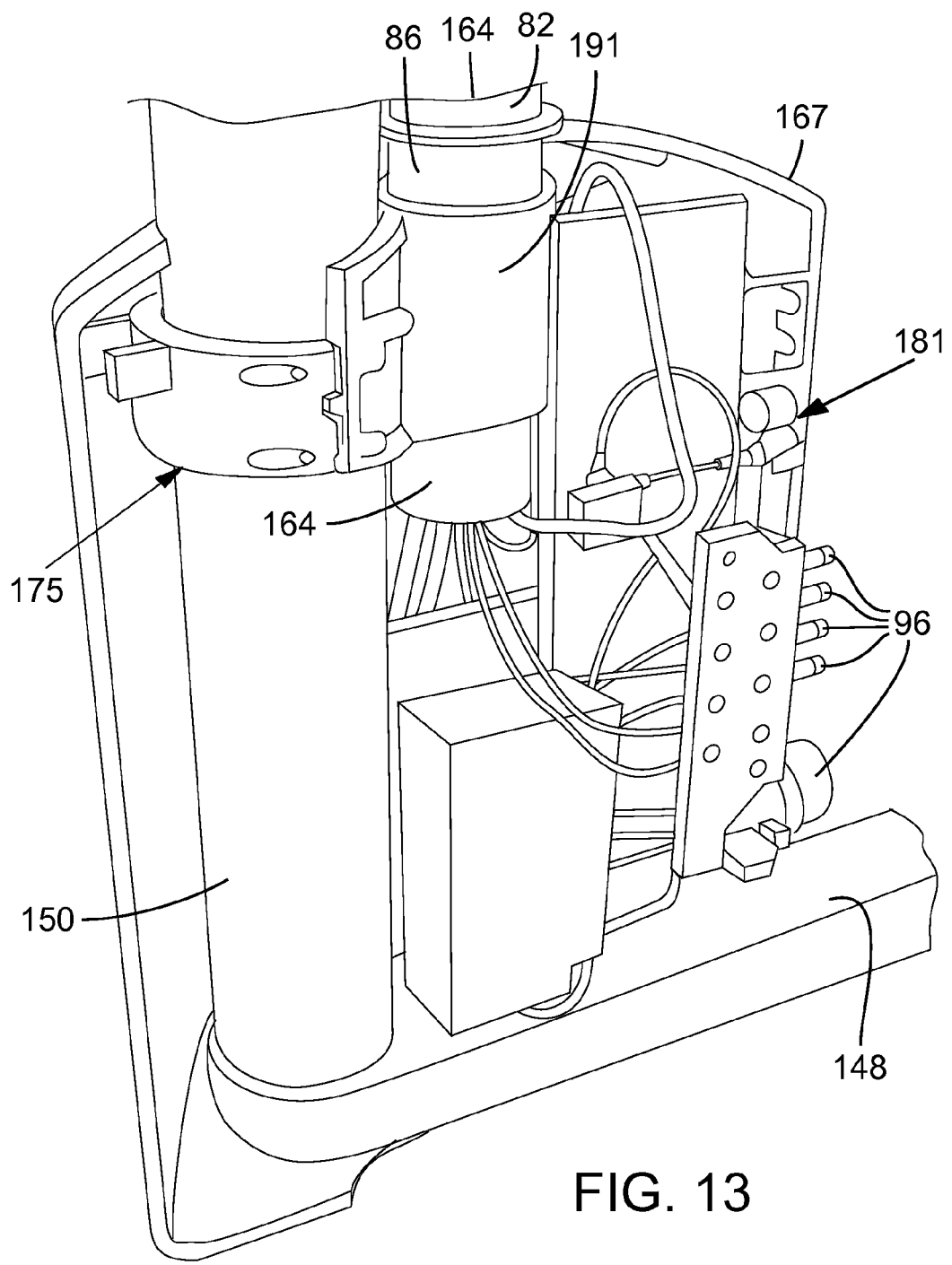
FIG. 13 is an enlarged elevational view of the rear mounted delivery system of FIG. 5 shown with a cover removed to expose an interior of the system.

FIG. 13 shows the rear delivery system 162 with a portion of the cover 167 removed to expose the interior 181. Within the interior 181, there is a main control unit having various pneumatic and electronic circuits used in controlling the various implements and/or other equipment, such as the chair, a cuspidor, etc. In addition, room is provided for positioning additional components in the event that other circuits are required, such as, e.g., an add-on oral camera. Manual controls 96 for the fluid or electrical systems can be provided on or extend from an outer surface of the cover 167.

In typical dental delivery systems, the control unit is placed within the cabinets and occupies space that could otherwise be used for storage. Positioning the main control unit of the rear mounted delivery system 162 external to the cabinetry, e.g., in a space between the support arm 148 and the first upright 150, frees up space within the cabinetry for storage of other systems, objects or supplies, such as an in-cabinet mounting for a dental rinse water supply bottle and a dental line cleaning system as will be described in more detail below.

Also shown in FIG. 13 is an optional method of coupling the second upright 164 to the first upright 150. A bracket 175 is mounted to the upright 150. The bracket 175 has a second upright receiving portion 191 extending laterally from the first upright 150. The second upright 164 can be secured within the second upright receiving portion 191, for example, by resting the bracket 86 on the receiving portion 191 such that the second upright is offset from and extends generally parallel to the first upright 150. The upright can be rotatable within and relative to the receiving portion 191 of the bracket 175.

Figure 14:
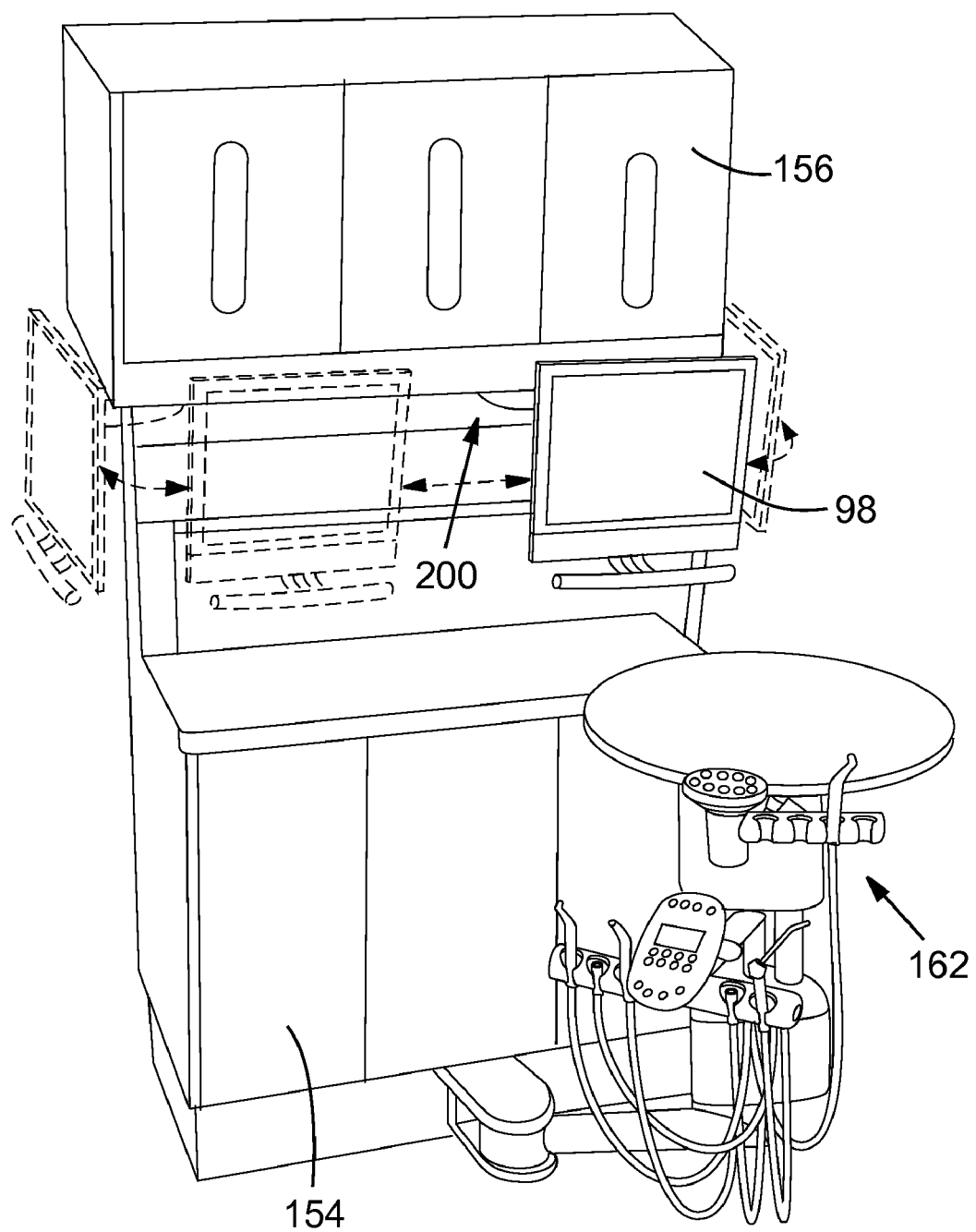
FIG. 14 is an elevational view of a monitor mount with an attached monitor suitable for use with a rear mounted delivery system.

FIG. 14 shows an optional monitor mount 200 with an attached monitor 98 suited for use with the rear delivery system. The monitor mount 200 can be coupled as shown to an underside of the upper cabinet 156. The monitor mount 200 provides a functional and aesthetically pleasing solution to laterally positioning the monitor at any position along the width between the ends of the cabinet (as shown in dashed lines), and also allows the monitor to be positioned "around the corners" of the cabinet (as shown in dashed lines). The angle of the monitor relative to a level axis can also be adjusted.

Figure 15:
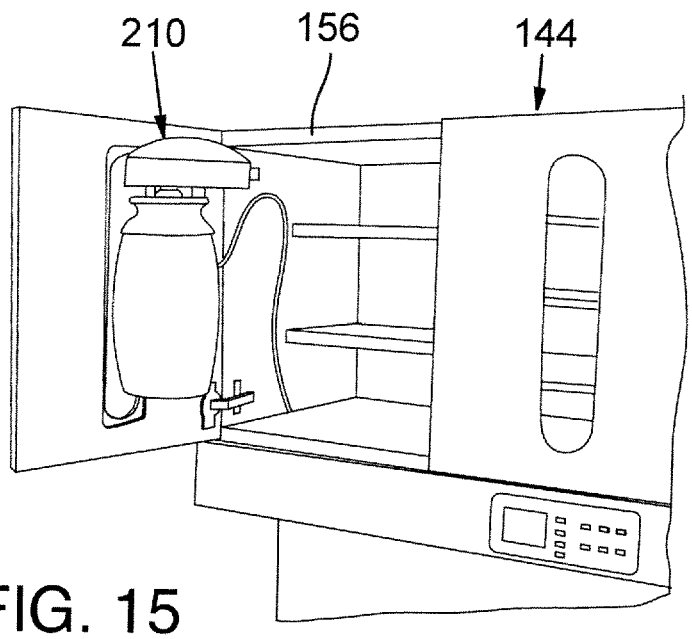
FIG. 15 is a perspective view of an in-cabinet mounting for a dental rinse water supply bottle suitable for use with a rear mounted delivery system.

FIG. 15 shows an optional in-cabinet mounting 210 for a dental rinse water supply bottle suited for use with a non-chair mounted delivery system. Use of the in-cabinet mounting 210 allows the water supply bottle to be moved from another location, e.g., attached to the dental chair or the delivery system, to the less obtrusive position within the cabinet 144.

FIG. 16 shows an optional dental line cleaning system 220 integrated in the cabinet. When activated with an attached line, the line cleaning system 220 dispenses a selected amount of cleaner into the line. In the exemplary implementation, the dental line cleaning system 220 includes three fittings (in three standard sizes) for coupling to cleaning lines 99 and injecting a cleaning fluid.

In view of the many possible embodiments to which the above principles may be applied, it should be recognized that the illustrated embodiments are only preferred examples and should not be taken as limiting the scope of the invention. Rather, the invention is intended to encompass all modifications, alternatives, and equivalents as may be included in the spirit and scope of the invention, as defined by the following claims.

We claim:

1. A rear dental delivery system for use with a reclining dental chair assembly, comprising:
    a cabinet with at least one cabinet door defining a vertical surface, the cabinet being positionable on or slightly above a floor upon which the dental chair assembly rests and at a location laterally spaced apart from the dental chair assembly when reclined;
    a stationary pivot connection configured to be stationarily mounted to the floor or the cabinet and positioned adjacent the vertical surface, wherein the stationary pivot connection defines a pivot axis and does not protrude above a level of a lower extent of the at least one cabinet door, thereby allowing the cabinet door to be opened without interference with the stationary pivot connection;
    at least one movable arm pivotably mounted to the stationary pivot connection, the movable arm having a distal end movable through an arc to define an operating range of the movable arm, the movable arm having a floor-level portion configured for positioning close to the floor;
    at least one upright member coupled to and extending upwardly from the at least one movable arm;
    a work surface coupleable to the upright member for positioning in a generally horizontal plane; and
    a leg and knee space defined, when the movable arm is pivoted away from the cabinet, in a vertical plane extending upwardly from the floor level portion of the movable arm to at least a level of an underside of the work surface, the leg and knee space having an upper unobstructed portion extending vertically between the work surface and the movable arm and extending laterally from the cabinet and through the pivot axis to the upright member,
    wherein the movable arm is pivotable toward the cabinet to provide access to open floor space separating the cabinet from the dental chair assembly.

2. The rear dental delivery system of claim 1, wherein the work surface is generally circular and pivotably coupled to the upright member at a pivot point spaced apart from a central axis of the work surface.

3. The rear dental delivery system of claim 2, further comprising an arm pivotably coupled to the work surface.

4. The rear dental delivery system of claim 3, further comprising a tool holder movably coupled to the arm.

5. The rear dental delivery system of claim 1, wherein at least a portion of a periphery of the work surface is curved, the work surface being pivotably coupled to the upright at a pivot point positioned near the periphery.

6. The rear dental delivery system of claim 5, further comprising an arm pivotably coupled to the work surface.

7. The rear dental delivery system of claim 6, further comprising a tool holder movably coupled to the arm.

8. The rear dental delivery system of claim 1, wherein the at least one upright member is a first upright member, the system further comprising a second upright member and an extension arm movably coupled to the second upright member, wherein the work surface is positionable at a level above the extension arm to allow the work surface and the extension arm to occupy vertical overlapping positions without interference.

9. The rear dental delivery system of claim 8, wherein the second upright member is positioned closer to the pivot connection than the first upright member.

10. The rear dental delivery system of claim 8, further comprising a tool holder movably coupled to the extension arm.

11. The rear dental delivery system of claim 8, wherein the second upright member is coupled to the first upright member at a point spaced above the at least one moveable arm.

12. The rear dental delivery system of claim 11, further comprising a housing that covers a junction between the at least one movable arm, the first upright member and the second upright member.

13. The rear dental delivery system of claim 11, wherein the second upright member is coupled to the first upright member in a spaced apart relationship via a bracket.

14. The rear dental delivery system of claim 1, wherein a distance between an upper surface of the at least one movable arm and a level of the floor is less than approximately 6 inches.

15. The rear dental delivery system of claim 1, further comprising an auxiliary tool holder selectively positionable along an edge of the work surface.

16. The rear dental delivery system of claim 1, further comprising a housing positioned adjacent a junction between the at least one movable arm and the upright member.

17. The rear dental delivery system of claim 1, further comprising water, air and vacuum connections extending through the pivot connection, the at least one movable arm and the upright member.

18. The rear dental delivery system of claim 1, wherein the stationary pivot connection is mountable to the floor and comprises an attachment portion configured for attachment to the floor with fasteners.

* * * * *